United States Patent [19]

Angstadt

[11] 4,104,310

[45] Aug. 1, 1978

[54] ORGANOMETALLIC COMPLEXES AS ALKYLAROMATIC OXIDATION CATALYSTS

[75] Inventor: Howard P. Angstadt, Media, Pa.

[73] Assignee: Sun Ventures, Inc., St. Davids, Pa.

[21] Appl. No.: 524,910

[22] Filed: Nov. 18, 1974

Related U.S. Application Data

[63] Continuation-in-part of Ser. No. 773,633, Nov. 5, 1968, abandoned.

[51] Int. Cl.² .......................................... C07C 179/04
[52] U.S. Cl. ................................................. 260/610 B
[58] Field of Search ....................... 260/610 B, 610 A Primary Examiner—James O. Thomas, Jr.
Assistant Examiner—Werren B. Lone
Attorney, Agent, or Firm—J. Edward Hess; Donald R. Johnson; Stanford M. Back

[57] ABSTRACT

Organometallic complexes formed between dialkylsulfoxides (DASO) and transition metal salts, including rare earth metals, have been found to be effective catalysts for the oxidation of olefins and secondary and tertiary alkylaromatics to form valuable oxidation products, particularly hydroperoxides, or their decomposition products.

13 Claims, No Drawings

ORGANOMETALLIC COMPLEXES AS ALKYLAROMATIC OXIDATION CATALYSTS

CROSS-REFERENCE TO RELATED APPLICATIONS

This application is a continuation-in-part of U.S. Ser. No. 773,633, filed Nov. 5, 1968, now abandoned.

This application is related to the following applications:

| SERIAL NO. | APPLICANT | FILE DATE |
| --- | --- | --- |
| 772,421 | Angstadt et al | 10/31/68 |
| 777,493 | Angstadt et al | 11/20/68 |
| 787,582 | Angstadt | 12/27/68 |
| 801,187 | Angstadt | 2/20/69 |
| 853,547 | Angstadt | 8/27/69 |

The entire disclosure of all of the above six cases is hereby incorporated herein by reference.

BACKGROUND OF THE INVENTION

This invention relates to a novel process for the oxidation of olefins and secondary and tertiary alkylaromatic hydrocarbons to form various oxidation products particularly, hydroperoxides, or the decomposition products thereof, i.e., alcohols, aldehydes, ketones and the like, or mixtures thereof. More particularly, this invention is directed to the use of complexes formed by reacting metal salts with dialkylsulfoxides (DASO) as oxidation catalysts in the aforesaid process, and especially those complexes formed between DASO and lanthanide metal salts. The term "lanthanide metal salts" is intended to include the metal lanthanum as well.

The oxidation of olefins and the alkyl side chains of aromatic compounds is already well known in the art. Thus, for example, it is known that tertiary alkylaromatics such as cumene can be auto-oxidized very slowly to form cumyl hydroperoxide when air or oxygen is rapidly passed through cumene warmed to about 80° C. Also, Canadian Pat. No. 510,517 teaches that the rate of oxidation of cumene can be enhanced when carried out in the presence of alkali or alkaline earth metal oxides or hydroxides, or in the presence of salts and oxides of heavy metals. Under these conditions, the conversion rate is only 2 to 3 percent per hour. Other oxidation catalysts are likewise well known, but in most instances, again, the conversion rate is low, as is the overall yield of the desired oxidation product.

It is an object of this invention, therefore, to provide a novel process for the oxidation of olefins and secondary and tertiary alkylaromatic compounds whereby, in particular, the oxidation rate, or the selectivity for hydroperoxide formation, or both, may be increased.

SUMMARY OF THE INVENTION

It has now been found, in accordance with the present invention, that organometallic complexes formed between metal salts, preferably those derived from transition metals (including metals of the lanthanide and actinide series), and dialkylsulfoxides are effective catalysts in the oxidation of olefins and secondary and tertiary alkylaromatic hydrocarbons. Certain of these catalysts, and particularly those derived from metal salts of the transition and lanthanide series, are especially effective in selectively forming the hydroperoxides to the substantial exclusion of hydroperoxide decomposition products.

DESCRIPTION OF THE PREFERRED EMBODIMENTS

The organometallic catalysts employed in the process of this invention, namely, the metal salt DASO complexes, may be represented by the general formula $$MX_n(DASO)_m$$

where M is a metal cation, preferably a transition metal from groups IIIB, IVB, VB, VIB, VIIB, VIIIB, IB, IIA or IIB of the periodic table, including the lanthanides and actinides; DASO is the aforementioned dialkylsulfoxide; X is the anion of the metal salt; $m$ is an integer of from 1 to 8; and $n$ is an integer of from 1 to 4. The alkyl moiety of the DASO may contain from 1 to 10 carbon atoms, preferably from 1 to 4 carbon atoms. Dimethylsulfoxide (DMSO) has been found to be especially useful in this invention, and although in the following description reference will be made to this particular compound, it will be understood to be representative of the DASO compounds generally.

These complexes may be prepared in accordance with the teachings of the *Inorg. Chem.*, 6, 1539 (1967) or *J. Inorg. Nucl. Chem.*, 16, 219 (1961) wherein is described the complexing of DMSO with the perchlorate or halide salts of zinc, cobalt, iron and the like. Briefly, the preparation of these compounds may readily be achieved by mixing a hydrate of the metal salt with an excess of DMSO and recovering the resultant crystals in a known manner. Alternatively, the complex may be prepared by first dissolving the metal salt in an excess of solvent, preferably an alkanol such as t-butanol, to which solution is added an excess of DMSO, followed by routine recovery and drying of the resulting precipitate. In some instances the complex does not form a solid which can be recovered readily, if at all, in which case the resulting solution may satisfactorily be employed instead. These organometallic complexes may be employed either as the purified solid or in solution with excess DMSO itself as the preferred solvent therefor.

Many of these DMSO metal complexes preferentially give yields of hydroperoxides to the exclusion of hydrocarbon decomposition products at conversion rates of at least about 4 percent per hour. In the case of those remaining metal complexes which yield little or no detectable amounts of hydroperoxides in the final product, but which do yield other oxidation products, this is because the hydroperoxides which are first formed are then rapidly decomposed by the catalyst complex itself to form aldehydes, alcohols, ketones or the like. Thus, in the case of the olefins, for example, where oxidation is effected as shown by O₂ uptake yet no hydroperoxide or minor amounts are found, there is also recovered in the reaction mixture the corresponding alcohol and/or ketonic olefins and the like.

That is to say, since the known mechanism for the autoxidation of alkyl aromatic compounds includes the homolytic cleavage of the first formed intermediate, i.e. the hydroperoxide, it is recognized that catalysts which accelerate this oxidation will also accelerate the decomposition of this intermediate. Hence it is possible to autoxidize the hydrocarbon to oxidized products without being able to detect the hydroperoxide intermediate because it is being decomposed to other oxidation products as rapidly as it is being formed. Therefore, the fact that no hydroperoxide is detected in the product does not mean it was not formed; it simply means that the catalyst is very effective in further converting this intermediate to aldehydes, ketones, alcohols, etc. In fact, the participation of hydroperoxides in the autoxidation of these hydrocarbons is so well established in the chemical literature that no other mechanistic pathways are seriously considered. See, for example, G. A. Russell J.A.C.S. 77, 4583–90, (1955); H. S. Blanchard, J.A.C.S. 82, 2014–21, (1959); J. A. Howard et al., *Canadian Jour. Chem.* 45, 785–792 (1966); inter alia.

Thus, it will be evident to those skilled in the art that the exact nature of the oxidation product can readily be determined by routine experimentation with various catalysts, but that in all cases it will be either an hydroperoxide and/or the decomposition products thereof as shown in the above-cited art, depending upon the exact catalyst composition chosen.

The metal salts used in forming the organometallic complexes are, as stated above, any metals of the periodic table, and preferably those derived from transition metals of groups IIIB, IVB, VB, VIB, VIIB, VIIIB, IB, IIA or IIB including the lanthanide and actinide metals.

The nature of the anion, X, is not critical, but may include any of the following inorganic or organic groups:

| | | | |
|---|---|---|---|
| $CN^-$ | cyanide | $AsO_3^{\equiv}$ | arsenite |
| $NC^-$ | isocyanide | $AsO_4^{\equiv}$ | arsenate |
| $CN_2^=$ | cyanamide | $C_2H_3O_2^-$ | acetate* |
| $OCN^-$ | cyanate* | $C_4H_4O_6^=$ | tartrate |
| $CNO^-$ | isocyanate* | $C_7H_5O_2^-$ | benzoate |
| $ClO^-$ | chlorite | $B_4O_7^=$ | tetraborate |
| $ClO_2^-$ | chlorate | $BrO_3^-$ | bromate |
| $SCN^-$ | thiocyanate | $Cr_2O_7^=$ | dichromate |
| $CNS^-$ | isothiocyanate | $F^-$ | fluoride |
| $SeCN^-$ | selenocyanate | $CH_2O^-$ | formate |
| $S_2O_3^=$ | thiosulfate | $SeO_3^=$ | selenide |
| $SO_3^=$ | sulfite | $SeO_4^=$ | selenate |
| $SO_4^=$ | sulfate | $C_6H_5O^-$ | phenoxide |
| $S^=$ | sulfide | $C_2O_4^=$ | oxalate* |
| $HS^-$ | hydrosulfide | $O^=$ | oxide |
| $TeCN^-$ | tellurocyanate | $TeO_3^=$ | tellurite |
| $OCl^-$ | oxychloride | $AsS_3^{\equiv}$ | thioarsenite |
| $OH^-$ | hydroxide | $AsS_4^{\equiv}$ | thioarsenate |
| $NO_2^-$ | nitrite* | $Cl^-$ | chloride* |
| $PO_3^{\equiv}$ | phosphite | $Br^-$ | bromide* |
| $PO_4^{\equiv}$ | phosphate* | $NO_3^-$ | nitrate* |
| $CrO_4^=$ | chromate | $CO_3^=$ | carbonate* |
| $BO_3^{\equiv}$ | borate | $ClO_4^-$ | perchlorate* | in which those marked with an asterisk are most preferred.

As mentioned hereinabove, the oxidation products of the instant process are hydroperoxides, or the decomposition products thereof, i.e., alcohols, aldehydes, ketones, epoxides or mixtures thereof. Of these various products, maximization of the formation of the hydroperoxides is generally preferred inasmuch as those compounds derived from the alkylaromatic compounds are especially useful as intermediates in the preparation of such products as phenols, naphthols, acetone and the like, while those derived from the olefins are useful in facilitating the drying capabilities of polymers, i.e., they are useful as siccative agents.

The olefins employed as the starting materials in this process include any straight or branched chain unsaturated compounds having at least one hydrogen atom on the α-carbon atom, such as octene-1, and the like, as well as cyclic olefins having at least one hydrogen atom on the α-carbon atom, such as cyclohexene, cyclooctadiene, α-pinene, dl-limonene and the like. These olefins may contain substituent groups which are nonreactive under the conditions of this process, as for example, ester, halo, nitro, alkyl or like groups which remain as substituents of the final product.

The secondary and tertiary alkylaromatic hydrocarbons employed as the starting materials in this process include compounds having the structural formula:

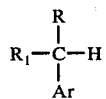

Wherein R is lower alkyl; $R_1$ is lower alkyl or hydrogen; Ar is substituted or unsubstituted aromatic nucleus such as phenyl or naphthyl; and wherein R and $R_1$ may be the same or different alkyl groups. The aromatic nucleus may be substituted by such groups as lower alkyl, lower alkoxy, halo, nitro or cyano radicals. Preferably, the secondary or tertiary alkylaromatic hydrocarbon is represented by such compounds as cumene, ethylbenzene, or sec.-butylnaphthalene, although it is understood that compounds such n-butylbenzene, sec.-butylbenzene, isopropylnaphthalene and the like may also be employed. It will be understood that by "secondary" is meant those compounds of the formula

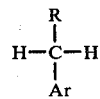

as defined above; while "tertiary" is intended to signify those compounds of the formula

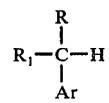

as defined above, wherein $R_1$ is alkyl.

The process of this invention is conveniently carried out by the rapid passage of air or oxygen through a suitable reactor, to which has first been added a solution of the alkylaromatic hydrocarbon and organometallic catalyst. The solvent for the reaction is preferably an excess amount of the alkylaromatic starting material, although other solvents which are inert to the reaction of peroxidation may likewise be employed.

The air or oxygen should be brought into intimate contact with the liquid phase with vigorous agitation either mechanically by the use of high speed stirrers, or by aeration using suitable nozzles or the like.

Mechanical agitation has been found to be particularly effective in those cases where the rate at which the oxygenating gas is introduced into the reactor is low, i.e., below about 3 liters per hour. Thus, for example, when air is merely introduced at the surface of the reaction mixture, agitation by a commercially available reciprocating disc type stirrer (e.g., "Vibro-Mixer," Chemapec Company, Inc., Hoboken, N.J.) has been found to increase the rate of oxidation per hour by as much as four-fold over what is obtained with lesser amounts of agitation.

Alternatively, these increased rates may similarly be achieved, and mechanical agitation substantially or entirely dispensed with by appreciably increasing the rate at which air or oxygen is introduced into the reaction medium. This is preferably accomplished by bubbling the oxygenating gas through the reaction mixture, vigorously, desirably in such a manner as to insure maximum dispersal of the gas through the medium, as for example, by using fritted glass discs or the like. Depending upon the amount of liquid medium involved, the rate of oxygenating gas may generally vary from about 3 to 300 liters per hour.

The amount of catalyst employed will vary depending upon the nature and amount of material to be oxidized and the nature of the catalyst itself. In general, however, from about 0.01 to 5.0 parts by weight of catalyst per 100 parts of substrate, and preferably from 0.2 to 1.0 parts per 100 parts has been found to be satisfactory.

The rate of input of oxygen or air will likewise vary depending upon the reaction temperature and pressure employed. There should be provided an amount at least theoretically sufficient to convert the alkyl aromatic compound to the corresponding hydroperoxide, and preferably an excess of this amount. In general, a flow rate ranging from 0.5 to 300 liters per hour is sufficient for most conversions, and preferably at least 3 liters per hour as described above. While the reaction is preferably carried out at atmospheric pressure, it is possible to employ an oxygen pressure of from about 0.2 atmospheres to 50 atmospheres, and preferably about 1 to 10 atmospheres. At these higher pressures the oxidation rate is found to increase substantially when the organometallic complexes are employed, and particularly those catalysts which are selective for hydroperoxide formation.

The reaction temperature may range from about 80° to 150° C, and preferably from 90° to 120° C. At temperatures above 150° C the catalysts tend to be thermally unstable.

The reaction is generally run for from half an hour to ten hours, depending upon the amount of substrate employed and the degree of conversion desired. When, however, a hydroperoxide is the principal product being formed, it is desirable that the reaction be terminated after a period of one to six hours at which point the reaction rate usually begins to taper off.

Advantageously, small amounts of the hydroperoxide corresponding to the desired product may be introduced into the reaction medium to act as a reaction initiator. Thus, for example, when cumene is being oxidized, it has been found to be advantageous to add small amounts of cumyl hydroperoxide in order to further accelerate the initial rate of reaction. The amount of hydroperoxide to be added is not critical, but 0.1 percent to 1.0 percent by weight of the starting material is preferred. It should be understood, however, that the addition of any such initiator will not change the nature of the product that would otherwise be obtained; the initiator serves only to reduce the induction time of the reactor.

The resulting products are readily recovered from the reaction medium by conventional methods. Thus, for example, a hydroperoxide may be conveniently recovered by isolating it as its sodium salt by addition of concentrated aqueous NaOH to the reaction product, followed by separation and drying of the hydroperoxide salt.

In the following examples, unless otherwise noted, both rate of conversion of the starting material and selectivity of the catalyst for converting the starting material to the corresponding hydroperoxide were measured. To measure rate of conversion, regardless of the nature of the oxidation product, the amount of oxygen uptake in a closed system was used as measure of the amount of oxidation which took place; to measure the amount of hydroperoxide formed, samples of the reaction medium were periodically withdrawn and iodometrically titrated to determine the hydroperoxide content. On the basis of both of these figures the selectivity of any given catalyst for the formation of hydroperoxide could then be routinely determined.

EXAMPLE 1

12.0 g. (100 m moles) of cumene were placed in a flask and rapidly stirred with 0.060 g. (~0.1 m mole) of $TiCl_4 \cdot DMSO$ complex in excess DMSO. The flask was immersed in a 100° C oil bath and oxygen opened to the system. Oxygen uptake began immediately. At the end of 2 hours, 6.7 percent of the cumene was converted to cumene hydroperoxide. In the absence of the catalyst only 2 percent of the cumene was converted.

EXAMPLE 2

Following the general procedure of Example 1, but substituting 30 mg. of lanthanum chloride DMSO catalyst complex in 7 drops of DMSO for the $TiCl_4 \cdot DMSO$ catalyst complex of Example 1, there was obtained the following results:

TABLE 1

| Time: | 1 hour | 2 hours | 3 hours | 4 hours |
| --- | --- | --- | --- | --- |
| Cumene Conversion | 2.64% | 9.47% | 15.4% | 19.6% |
| Hydroperoxide Yield | 4.28% | 11.4% | 17.9% | 20.2% |
| Selectivity | >100% | >100% | >100% | 100% |

EXAMPLE 3

Following the general procedures of Example 1 but substituting sec.-butylnaphthalene for the cumene of that example, sec.-butylnaphthalene hydroperoxide is obtained in good yield.

EXAMPLE 4

In an 80 ml. Morton flask equipped with a hollow shafted stirrer and fitted with a dry-ice condenser is placed 18.4 g. (100 m moles) of -sec.-butylnaphthalene, 60 mg. of $NiCl_2 \cdot DMSO$ and 0.2 cc of cumene by hydroperoxide. Oxygen is passed through the system with rapid stirring at the rate of 60 ml./minute. The product, a white solid collected on a dry-ice cold finger, is identified as acetaldehyde by a comparison of the properties of its 2,4-di-nitrophenylhydrazone with an authentic sample.

EXAMPLE 5

8.2 g. (100 m moles) of cyclohexene is placed in a flask and rapidly stirred by a Vibro-Mixer with 40 mg. of $MnBr_2 \cdot DMSO$ and 0.2 cc of cumene hydroperoxide. The flask is immerssed in a 60° C oil bath, connected to an oxygen buret and the oxygen opened to the system. At the end of two hours cyclohexene hydroperoxide has been formed in good yield as determined by $O_2$ volume consumed and iodometric titration.

When α-pinene and cyclooctadiene are individually substituted for cyclohexene in the foregoing procedure, there are obtained the corresponding α-pinene hydroperoxide and cyclooctadiene hydroperoxide, respectively.

EXAMPLE 6

The procedure of Example 5 is repeated except that 50 mg. of LaCl$_3$·DMSO is substituted for the corresponding manganese bromide complex of Example 5 and the methyl ester of linoleic acid is substituted for cyclohexene. The product contains not only the corresponding hydroperoxide of the acid ester in good yield, but also a mixture of the corresponding unsaturated ketonic and alcoholic esters.

EXAMPLE 7

Following the procedure of Example 5, but using methylcyclohexene and Mn(NO$_3$)$_2$·DMSO as the substrate and catalyst, there is obtained after 1 hour at 75° C a good yield of methylcyclohexene hydroperoxide along with small amounts of methylcyclohexenol and methylcyclohexenone.

EXAMPLE 8

Following the procedure of Example 5, but using cobalt acetate·DMSO complex as the catalyst, good rates of conversion of the cyclohexene into a mixture of cyclohexenol and cyclohexenone are obtained. These are further oxidation products of the first formed hydroperoxide.

EXAMPLE 9

Following the procedure of Example 5, but using tetralin as the substrate and CrCl$_3$·DMSO as the catalyst, a 5% per hour rate of conversion during the 2 hours of the experiment is obtained. A high yield of tetralin hydroperoxide is obtained along with small amounts (less than 10%) of tetralone.

The invention claimed is:

1. In the process for the catalytic oxidation of aliphatic or alicyclic olefins having at least one hydrogen atom on the α-carbon atom, said olefins having from 3 to 19 carbon atoms, or secondary or tertiary alkylaromatic hydrocarbons of the formula

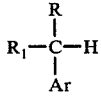

wherein R is lower alkyl; R$_1$ is lower alkyl or hydrogen; and Ar is an aromatic nucleus selected from the group consisting of phenyl and naphthyl, in the presence of air or oxygen at a temperature of from about 80° to 150° C to form hydroperoxides, the decomposition products thereof, or mixtures of the same, the improvement wherein the catalyst is of the formula

wherein DASO is a dialkylsulfoxide, the alkyl moiety of which has from one to four carbon atoms; MX is a metal salt wherein M is a transition metal cation of Group IB, IIB, IIIB, IVB, VB, VIB, VIIB, VIIIB or IIa of the Periodic Table and X is the anion of said metal salt; $m$ is an integer of from 1 to 8; and $n$ is an integer of from 1 to 4, wherein the ratio of said catalyst to said olefin or alkylaromatic hydrocarbon is from about 0.01 to 5.0 parts by weight of catalyst per 100 parts by weight of olefin or alkylaromatic hydrocarbon.

2. The process according to claim 1 wherein the dialkylsulfoxide is dimethylsulfoxide.

3. The process according to claim 1 wherein the reaction is carried out at a temperature of from 90° to 120° C.

4. The process according to claim 1 wherein the metal is of the lanthanide or actinide series.

5. The process according to claim 1 wherein the alkylaromatic compound is cumene, the catalyst is dimethylsulfoxide and a lanthanide metal salt, and the product consists substantially of cumyl hydroperoxide.

6. The process according to claim 1 wherein the oxidation is carried out in the added presence of a hydroperoxide initiator.

7. The process according to claim 1 wherein the reaction is carried out under vigorous agitation.

8. The process according to claim 1 wherein the oxygen is introduced at a rate of from about 0.5 to 300 liters per hour.

9. The process according to claim 1 wherein the oxidation is carried out at an oxygen pressure of from 1 to 50 atmospheres.

10. The process according to claim 1 wherein the anion is a bromide, chloride, carbonate, nitrate or perchlorate.

11. The process according to claim 1 wherein the anion is a cyanide, cyanate, isocyanate, nitrite, phosphate, acetate or oxalate.

12. The process according to claim 1 wherein the hydroperoxide decomposition products are alcohols, aldehydes, ketones, or mixtures thereof.

13. The process according to claim 1 wherein the ratio of catalyst to substrate is in the range of from 0.5 to 1.5 parts by weight of catalyst per 100 parts of substrate.

* * * * *